(12) United States Patent
Yi et al.

(10) Patent No.: US 9,326,839 B2
(45) Date of Patent: May 3, 2016

(54) INFRA-OBTURATOR TENSION TRANSFER DEVICE

(76) Inventors: Jeong Yoon Yi, Daejeon (KR); Hwa Jeong Yi, Daejeon (KR); Su Ho Yi, Daejeon (KR)

( * ) Notice: Subject to any disclaimer, the term of this patent is extended or adjusted under 35 U.S.C. 154(b) by 214 days.

(21) Appl. No.: 13/132,849

(22) PCT Filed: Mar. 7, 2011

(86) PCT No.: PCT/KR2011/001568
§ 371 (c)(1),
(2), (4) Date: Jun. 3, 2011

(87) PCT Pub. No.: WO2011/108911
PCT Pub. Date: Sep. 9, 2011

(65) Prior Publication Data
US 2011/0257470 A1      Oct. 20, 2011

(30) Foreign Application Priority Data

Mar. 5, 2010   (KR) .................. 10-2010-0019829
Mar. 7, 2011   (KR) .................. 10-2011-0020122

(51) Int. Cl.
*A61F 2/04*   (2013.01)
*A61F 2/00*   (2006.01)

(52) U.S. Cl.
CPC .................. *A61F 2/0045* (2013.01)

(58) Field of Classification Search
CPC ..................... A61F 2/00; A61F 2/02
USPC ............ 600/29–31, 37; 606/151; 623/23.64, 623/23.66, 23.67; 128/885
See application file for complete search history.

(56) References Cited

U.S. PATENT DOCUMENTS

| | | | |
|---|---|---|---|
| 5,123,428 A | 6/1992 | Schwarz | |
| 5,785,640 A | 7/1998 | Kresch et al. | |
| 6,221,005 B1* | 4/2001 | Bruckner et al. | 600/30 |
| 2003/0062052 A1 | 4/2003 | Carter et al. | |
| 2005/0261547 A1* | 11/2005 | Bouffier | 600/37 |

(Continued)

FOREIGN PATENT DOCUMENTS

| | | |
|---|---|---|
| CN | 101626791 A | 1/2010 |
| KR | 10-0613331 B1 | 8/2006 |

(Continued)

OTHER PUBLICATIONS

International Search Report issued in International Application No. PCT/KR2011/001568 on Nov. 23, 2011, 2 pages.

*Primary Examiner* — Christine H Matthews
(74) *Attorney, Agent, or Firm* — Rothwell, Figg, Ernst & Manbeck, P.C.

(57) ABSTRACT

Disclosed is a tension delivery device for preventing urinary incontinence, which includes: Retzius space-insertion portions which are respectively to be inserted into the Retzius spaces positioned on the left side and right side of the urethra and move in response to the pressure or the Retzius spaces; and a urethral support portion which extends convergently from the Retzius space-insertion portions and serves to support the urethra upward, wherein the lateral cross section of the urethral support portion becomes thinner from Retzius space-insertion portions toward the distal end, and a mesh structure may be provided along the outer surface of the tension transfer device. The device can sufficiently inhibit urinary incontinence, and is minimally invasive so that damage associated with an invasive method can be reduced.

15 Claims, 7 Drawing Sheets

(56) References Cited

U.S. PATENT DOCUMENTS

| | | | |
|---|---|---|---|
| 2006/0195011 A1* | 8/2006 | Arnal et al. | 600/37 |
| 2007/0156012 A1 | 7/2007 | Tracey et al. | |
| 2008/0200751 A1* | 8/2008 | Browning | 600/30 |
| 2009/0082617 A1* | 3/2009 | Vecchiotti et al. | 600/30 |
| 2009/0259094 A1* | 10/2009 | Bouchier et al. | 600/37 |
| 2011/0004049 A1 | 1/2011 | Yi et al. | |

FOREIGN PATENT DOCUMENTS

| | | |
|---|---|---|
| KR | 10-0947552 B1 | 3/2010 |
| WO | 00/36996 A1 | 6/2000 |
| WO | 2008/107483 A2 | 9/2008 |

* cited by examiner

INFRA-OBTURATOR TENSION TRANSFER DEVICE

CROSS REFERENCE TO RELATED APPLICATIONS

This application is a 35 U.S.C. §371 National Phase Entry Application from PCT/KR2011/001568, filed Mar. 7, 2011, and designating the United States, which claims priority under 35 U.S.C. §119 to Korean Patent Application No. 10-2010-0019829 filed on Mar. 5, 2010 and to Korean Patent Application No. 10-2011-0020122 filed on Mar. 7, 2011, which are incorporated herein in their entireties.

TECHNICAL FIELD

The present invention relates to an infra-obturator tension transfer device (IOT), which is inserted into the human body by incising a minimum area of the region beneath the urethra, for example, and inserting the Retzius space-insertion portions thereof into the Retzius spaces, and can induce the tension of the muscles around the urethra when abdominal pressure increases, thereby inhibiting urinary incontinence. When the tension transfer device of the present invention is combined with a mesh structure, it can usually prevent urinary incontinence caused by muscular relaxation.

BACKGROUND ART

Urinary incontinence is the involuntary leakage of urine. Urinary incontinence symptom occurs when abdominal pressure increases due to physical exercise, moving, laughing or coughing. Urinary incontinence may be caused by aging, pregnancy, childbirth, chronic cough, asthma, excessive exercise, or the like, and may get worse due to weight gain or menopause. Such urinary incontinence usually occurs when urethral sphincters for supporting the urethra and the urinary bladder are weakened.

Various technologies for treating such urinary incontinence are disclosed in a plurality of documents, including U.S. Pat. No. 6,808,485, Japanese Unexamined Patent Publication No. 1998-155897, and Korean Unexamined Patent Publication No. 2003-34218, which propose to insert an elastic material into the vaginal canal, or to inject hydrogel particles (polymer) into tissues around the urethra or the ureter.

Recently, urinary incontinence has been treated by supporting the suburethra (the bottom area of the urethra), wherein the suburethra is supported by forming a passage through the suburethra from an inguinal region using a guide needle holder, and then supporting a prolene mesh (or in the reversed sequence) by the guide needle holder.

However, the recent urinary incontinence treatment procedure typically requires spinal anesthesia or sedative anesthesia, although the treatment procedure is the minimal invasive surgery procedure among the existing ones, and may cause damage to muscles, ligaments, and blood vessels in the route: the inguinal region→the obturator foramen→the suburethra. For this reason, the possibility of damaging other anatomical structures or propagating inflammation is high. Furthermore, adhesion of the mesh after surgery makes it difficult to perform surgery again, and it is impossible to remove the mesh. In addition, a device that causes damage, e.g. a guide needle holder, is needed.

DISCLOSURE

Technical Problem

The present invention has been made in view of the above-mentioned problems occurring in the prior art, and it is an object of the present invention is to provide a tension transfer device, which is inserted into the human body by incising a minimum area of the region beneath the urethra, for example, and inserting the Retzius space-insertion portions thereof into the Retzius spaces, and can induce tension of the muscles around the urethra when abdominal pressure increases, thereby automatically inhibiting urinary incontinence.

Another object of the present invention is to provide a tension transfer device which includes a mesh structure provided along the outer surface of the tension transfer device so that the mesh structure is adsorbed onto human tissue when the device is implanted into the human body, whereby the device can continuously tense the muscles around the urethra, thereby usually preventing involuntary urinary incontinence caused by muscular relaxation.

Technical Solution

To achieve the above objects and other objects, in accordance with a first aspect of the present invention, there is provided an infra-obturator tension transfer device comprising: a urethral support portion which serves to support the urethra upward and is formed such that the lateral cross section thereof becomes thinner toward the distal end; neck portions extending from both sides of the urethral support portion to Retzius spaces; and Retzius space-insertion portions which are respectively to be inserted in the Retzius spaces positioned on the left side and right side of the urethra and serve to transfer a rotating force to the neck portions in response to the pressure of the Retzius spaces so that the urethral support portion moves upward toward the urethra, the Retzius space-insertion portions each having an elasticity-attenuating opening so as to attenuate the upper and lower oscillation of the Retzius spaces.

According to the present invention, each of the Retzius space-insertion portions preferably protrudes toward the front of the Retzius spaces.

Also, the tension transfer device is made of a biocompatible solid material. Any person of ordinary skill in the art can appreciate that any material may be used as the solid material of the tension transfer material in the present invention, as long as it satisfies the requirements for the physical properties of the solid material of the tension transfer device and has little or no side effects when it is inserted into the human body. Alternatively, the tension transfer device may be formed in such a manner that a fluid material is filled therein. Examples of the fluid material include air, saline and cohesive gel.

In accordance with a second embodiment of the present invention, there is provided an infra-obturator tension transfer device comprising: a urethral support portion which serves to support a urethra upward and is formed such that the lateral cross section thereof becomes thinner toward the distal end; neck portions extending from both sides of the urethral support portion to Retzius spaces; and elasticity-attenuating portions which are respectively to be inserted in the Retzius spaces positioned on the left side and right side of the urethra and serve to transfer a rotating force to the neck portions in response to the pressure of the Retzius spaces so that the urethral support portion moves upward toward the urethra, the elasticity-attenuating portions each having a flat hook shape so as to attenuate the upward and downward oscillation of the Retzius spaces.

In accordance with a third embodiment of the present invention, there is provided a urethral support portion which serves to support a urethra upward and is formed such that the lateral cross section thereof becomes thinner toward the distal end; neck portions extending from both sides of the urethral support portion to Retzius spaces; Retzius space-insertion portions which are respectively to be inserted in the Retzius spaces positioned on the left side and right side of the urethra and serve to transfer a rotating force to the neck portions in response to the pressure of the Retzius spaces so that the urethral support portion moves upward toward the urethra, the Retzius space-insertion portions each having an elasticity-attenuating opening so as to attenuate the upward and downward oscillation of the Retzius spaces; and a mesh structure which surrounds the backside of the urethral support portion and each of the neck portions in a 'U' shape and is partially thermally bonded to the backside of the urethral support portion and each neck portion; wherein the lateral cross section of the urethral support portion becomes thinner from the Retzius space-insertion portion to the distal end.

Advantageous Effects

According to the tension transfer device of the present invention, when a urinary incontinence patient exercises, sneezes or coughs to increase the abdominal pressure instantaneously, the urethral support portion can press the urethra portion upward due to the increase in pressure of the Retzius spaces, thereby sufficiently inhibiting urinary incontinence. Also, according to the present invention, a mesh structure is provided along the outer surface of the tension transfer device, whereby the tension of the muscles around the urethra can be usually induced, thereby inhibiting involuntary urinary incontinence caused by muscular relaxation.

Furthermore, the tension transfer device according to the present invention does not require a guide needle holder that causes damage, and is minimally invasive so that damage associated with an invasive method can be reduced. Thus, it eliminates the needs for spinal anesthesia, sedative anesthesia or the like and does not cause discomfort that can occur when excessive local anesthesia is performed.

In addition, the tension transfer device of the present invention can be easily corrected in a non-invasive manner when the therapeutic effect thereof is insufficient. Also, it is easily removed so that it makes it possible to perform surgery again using other methods when the therapeutic effect thereof is insufficient. In addition, the device makes it possible to shorten surgical time, reduce surgical complications and side effects, reduce surgical costs, and substitute for expensive imported surgical materials to reduce costs.

BRIEF DESCRIPTION OF THE DRAWINGS

The foregoing and other objects, features and advantages of the present invention will become more apparent from the following detailed description when taken in conjunction with the accompanying drawings in which.

BEST MODE

Mode for Invention

Figure 12:
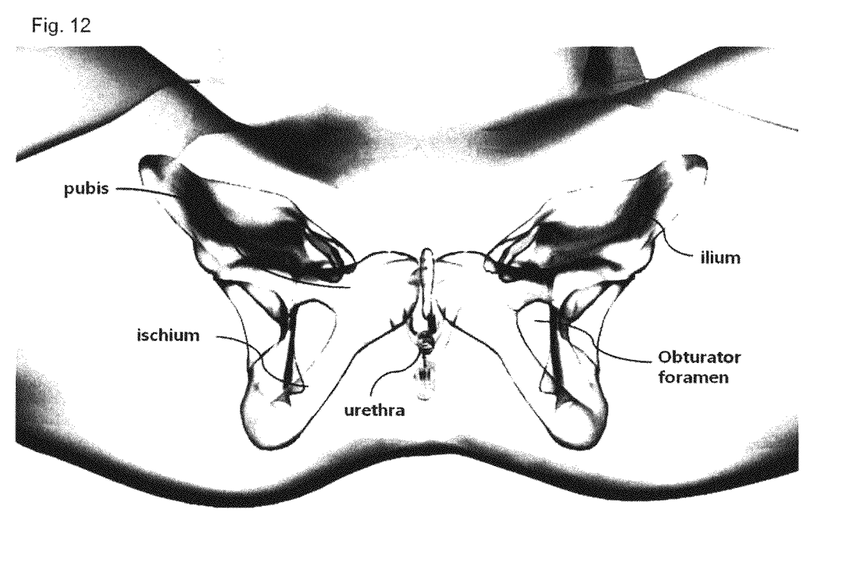
FIG. 12 is a view provided to further describe the implantation of the tension transfer device of the present invention.

As used herein, the term "obturator foramen" refers to a closed space as shown in FIG. 12, and was named because it is a closed circular space defined by a bone. The obturator foramen is located between the pubis and the ischium, and the reproductive organs including the bladder and the urethra are located behind the pubis and the ischium. Between the reproductive organs and the pubis, the Retzius space is located.

Thus, the tension transfer device according to the present invention is a structure which is located beneath the urethra while being inserted into the Retzius spaces.

Hereinafter, the present invention will be described in further detail with reference to the accompanying drawings.

Figure 1:
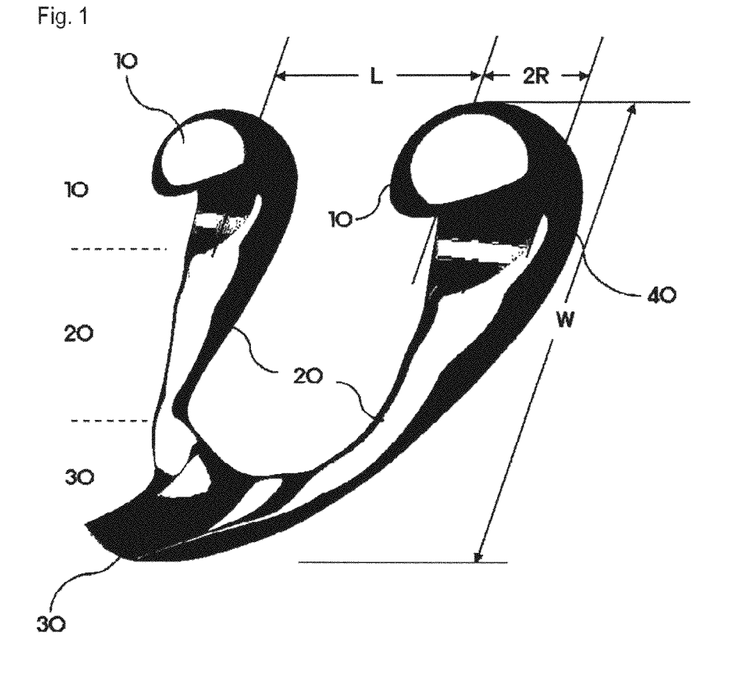
FIG. 1 is a perspective view of a tension transfer device according to a first embodiment of the present invention.
Figure 2:
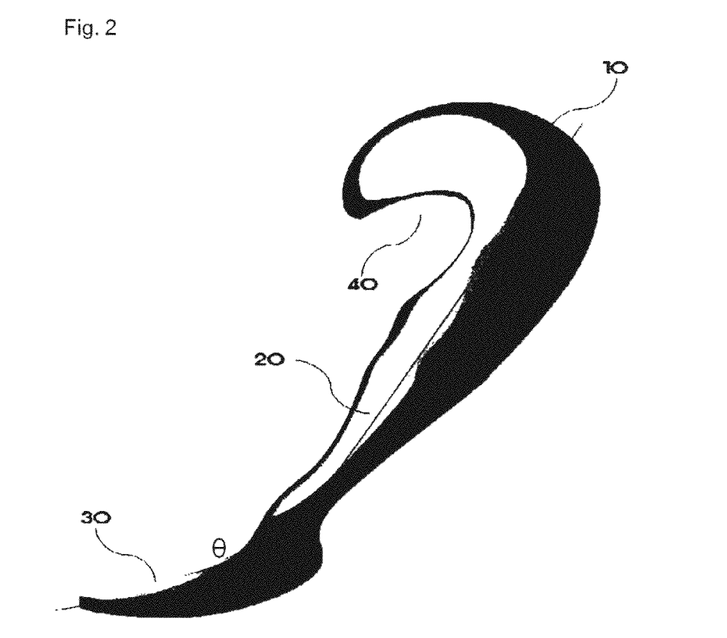
FIG. 2 is a side view of the tension transfer device shown in FIG. 1.

FIG. 1 is a schematic perspective view of a tension transfer device according to a preferred embodiment of the present invention, and FIG. 2 is a side view of the tension transfer device shown in FIG. 1.

As shown in FIGS. 1 and 2, a tension transfer device according to a first embodiment of the present invention includes: a urethral support portion 30 which serves to support the urethra upward and is formed such that the lateral cross section thereof becomes thinner toward the distal end; neck portions 20 extending from both sides of the urethral support portion to Retzius spaces; and Retzius space-insertion portions 10 which are respectively to be inserted in the Retzius spaces positioned on the left side and right side of the urethra and serve to transfer a rotating force to the neck portions in response to the pressure of the Retzius spaces so that the urethral support portion moves upward toward the urethra, the Retzius space-insertion portions each having an elasticity-attenuating opening 40 so as to attenuate the upper and lower oscillation of the Retzius spaces.

The urethral support portion 30 serves to support the urethra upward and has a concave shape so that it is curved downward. However, the urethral support portion 30 may either have a convex shape so as to be curved upward or have a flat shape having no curvature.

Meanwhile, as shown in the figures, the Retzius space-insertion portions 10 are respectively inserted in the Retzius spaces positioned on the left and right sides of the urethra 100.

Although two Retzius space-insertion portions 10 are illustrated in this embodiment in consideration of the Retzius spaces positioned on the left and right sides of the urethra, the number of the Retzius space-insertion portions will not be limited, as long as they can follow the movement of the Retzius spaces or follow the deformation of the muscles beneath the urethra. Also, as shown in the figures, the Retzius space-insertion portions 10 are preferably shaped such that the protrusion thereof can be supported at the interior edge of the ischial ramus in the Retzius space.

As shown in the figures, the Retzius space-insertion portions 10 having a branched shape converge centrally to form the urethral support portion 30 which will be located under the urethra after implantation thereof. This urethral support portion 30 will move with the increase in pressure of Retzius space increases caused by an increase in abdominal pressure and/or with the increase in muscular pressure around the urethra, so that it will support the urethra upward.

The principle and specific description thereof will be given below.

The Retzius space-insertion portions 10 have a spherical shape, but may include a hook-shaped groove 40 at a connection with a neck portion 20, in which the hook-shaped groove 40 serves to prevent the Retzius space-insertion portion 10 from being released from the Retzius space. If necessary, the hook-shaped groove 40 can be fixed to one side of the ischial ramus.

Meanwhile, as shown in FIGS. 1 and 2, particularly FIG. 2, the side or lateral cross-section of the urethral support portion 30 is formed such that it becomes thinner from the Retzius space-insertion portion 10 toward the distal end, that is, the lower end of the left side of FIG. 2, and smoothly supports the urethra upward. A connection between the Retzius space-insertion portion 10 and the urethral support portion 30 preferably has a neck portion 20 having a size smaller than that of the Retzius space-insertion portion 10.

As the two Retzius space-insertion portions 10 are placed horizontally in the two Retzius spaces, respectively, the Retzius space-insertion portions 10 can be formed such that they are suitably placed or inserted in the Retzius spaces. This is because the sizes of the Retzius spaces vary depending on subjects. In view of this fact, in the present invention, the Retzius space-insertion portions 10 can be designed to have a size of 5-40 mm. However, the diameter (2R) of the Retzius space-insertion portions 10 may preferably be 8-11 mm.

Also, the length (L) between the two Retzius space-insertion portions 10 may be 1-100 mm, and preferably 18-24 mm. Also, the width (W) between the end of any one of the Retzius space-insertion portions 10 and the end of the urethral support portion 30 is 10-80 mm, and preferably 30-35 mm. This tension transfer device is made of a silicone elastic material, an elastic material harmless to the human body, or a sheath material containing a flexible material, and has a hardness of about 10-90 Ha, and preferably about 70 Ha. In this regard, the hardness is a value measured by a Shore A hardness tester (Model LX-A Shore DUROMETER), and the hardness of 70 Ha corresponds to 1.925 N (=202.125 g·cm/s$^2$).

The hardness of silicone is an experimentally determined value that maintains psychological stability by offsetting sensations caused by adhesion of the silicon to human tissue when the silicon is inserted into the human body. Thus, the hardness of silicon can be suitably selected within the range in which it is harmless to the human body.

The urethral support portion 30 is formed such that the length between the end thereof and the neck portion 20 is 9-11 mm and the width thereof is 7-9 mm. Also, the urethral support portion is extruded such that the thickness thereof is decreased in the protrusion direction so as to enhance the force for supporting the urethra. Furthermore, the urethral support portion 30 is formed to have a downwardly concave surface so as to stably support the urethra.

The concave structure of the urethral support portion 30 has a radius of 47-57 mm with respect to the side cross section, and preferably 52 mm with respect to the side cross section. The concave structure of the urethral support portion 30 serves to support the urethra upward so that the elasticity thereof is usually maintained.

Meanwhile, the neck portion 20 extends from each Retzius space-insertion portion 10 so as to be bound with the side of the urethral support portion 30. In this regard, the upper end of the neck portion 20, which extends from the Retzius space-insertion portion 10, preferably has a diameter of 6-8 mm, and the lower end of the neck portion 20, which is bound with the urethral support portion 30, preferably has a diameter of 1.5-2.5 mm. However, the length of the neck portion can change in proportion to the sizes of the Retzius space-insertion portions and the interval therebetween.

As shown in FIG. 2, the neck portion 20 and urethral support portion 30 of the tension transfer device maintains a slope (θ) of 120-140°, but it is to be understood that they can be formed at an angle of 30-170° in consideration of elasticity.

Figure 3:
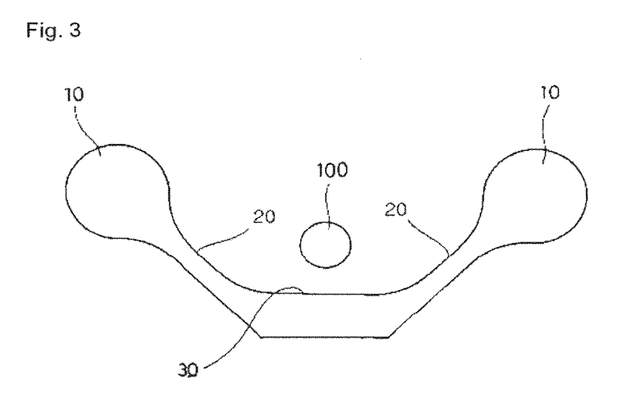
FIG. 3 is a front view of the tension transfer device shown in FIG. 1, which shows the positioning of the device according to the position of the urethra.

The above-described tension transfer device according to the first preferred embodiment of the present invention is inserted into the body of a patient as shown in FIG. 3. Specifically, the Retzius space-insertion portions 10 are respectively inserted into the Retzius spaces positioned on the left and right sides of the urethra, and thus the urethral support portion 30 is arranged so that it can support the urethra upward.

Figure 4:
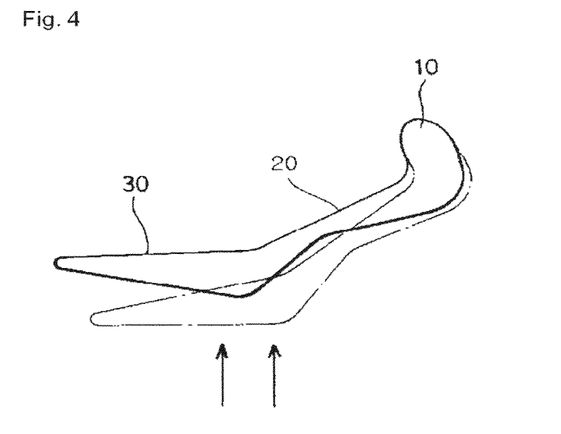
FIG. 4 imaginatively shows that, when the tension transfer device according to the first embodiment of the present invention is made of a solid material, it moves as abdominal pressure increases.
Figure 5:
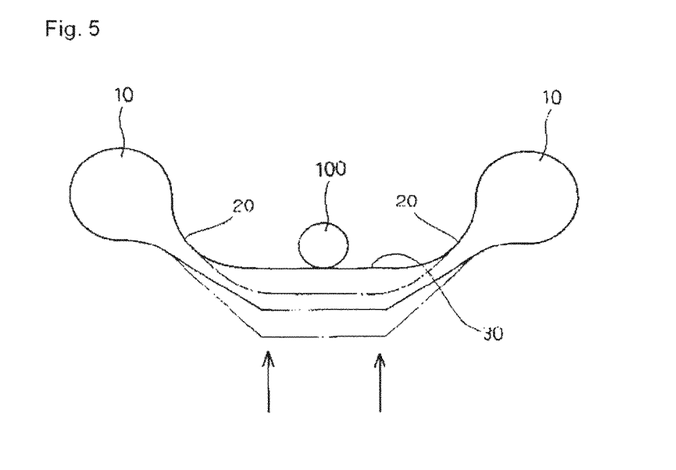
FIG. 5 is a front view of the tension transfer device shown in FIG. 4, which shows that the tension transfer device supports the urethra upward as abdominal pressure increases.

FIGS. 4 and 5 show that, when the tension transfer device having the above-described configuration is made of a solid material, it moves as abdominal pressure increases.

When a urinary incontinence patient sneezes or coughs, for example, the abdominal pressure increases, and thus the pressure of the Retzius spaces positioned on the left and right sides of the urethra also increases. At the same time, the muscles around the urethra tense so that the pressure thereof increases.

At this time, the Retzius space-insertion portions 10 located in the Retzius spaces serve as a rotating shaft that is fixed to the Retzius space due to contraction of the Retzius space. At the same time, as shown in FIG. 4, the urethral support portion 30 receives an upward force as the muscles under the urethra tense. In this regard, the pressure that is applied to the urethral support portion 30 varies depending on the shape of the urethral support portion 30. Namely, the portion indicated by the arrow in FIG. 4 receives the greatest pressure, and thus the urethral support portion 30 is lifted up using the Retzius space-insertion portions as rotating shafts. As the urethral support portion 30 is lifted up, it supports the urethra 100 upward as shown in FIG. 5.

Figure 6A:
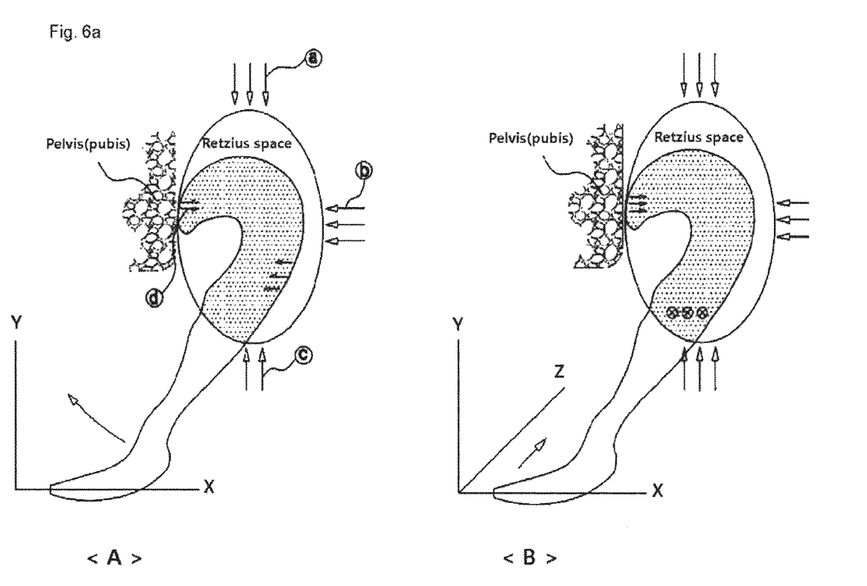
FIGS. 6a and 6b are view illustrating the main operational principle of the tension transfer device according to the first embodiment of the present invention.

Specifically, as shown in FIG. 6a, when a urinary incontinence patient exercises, sneezes, coughs or laughs, for example, the abdominal pressure increases, and thus the pressure of the Retzius spaces positioned on the left and right sides of the urethra also increases. At the same time, the muscles around the urethra also tense so that the pressure thereof increases. The muscular tension caused by abdominal pressure contracts the Retzius spaces, and thus presses the front upper portion and the back side of the Retzius space-insertion portions 10 placed in the Retzius spaces.

As shown in "A" of FIG. 6a, the neck portion 20 is pressed in the direction from the x-axis to the y-axis with respect to the front upper portion of the Retzius space-insertion portion 10. As a result, the urethral support portion 30 rotates clockwise.

Specifically, if the Retzius space located between the pelvis (pubis) and the bladder is contracted in the x and y-directions, the Retzius space will be pressed at a certain position of the pelvis. That is, the contact point between the pelvis and the Retzius space acts as a hinge point, and due to the pressure that is applied downward to the Retzius space, the urethral support portion 30 rotates clockwise.

As shown in "A" of FIG. 6a, when the muscles contract, external pressures of ⓐ, ⓑ and ⓒ are applied to the Retzius space. In this regard, the forces corresponding to the pressures ⓐ and ⓑ are substantial forces caused by the muscles, and the force corresponding to ⓒ is an indirect force caused by muscular contraction. Thus, the forces ⓐ and ⓒ are somewhat offset, and then the downward pressure remains. Also, the force ⓑ is attenuated by action and reaction (force corresponding to ⓓ) for the pelvis (pubis).

However, an external force such as the force ⓑ acts between the Retzius space-insertion portion 10 and the neck portion 20 or on a part of the neck portion 20. As a result, the force ⓑ acts in the negative (−) direction of the x-axis, while the forces ⓐ and ⓒ act in the negative (−) direction of the y-axis from the composition of forces. Thus, the Retzius space-insertion portions 10 receive a force in the direction of the left and down side of the figure. Also, as the contact point between the Retzius space-insertion portion 10 and the pelvis (pubis) acts as a hinge point, the neck 20 rotates clockwise in the figure.

In addition to this rotating force, as shown in "B" of FIG. 6a, an external force that presses the outer portion of the neck 20 can partially exist, which can add a force that rotates the urethral support portion 30, extending to the neck portion 20, in the direction from the x-axis to the z-axis. Thus, with this operational principle, the urethral support portion 30 having a concave curved portion will press the urethra upward and prevent urinary incontinence due to the force for supporting the urethra upward.

The reason why this operation is possible is because the material of the above-described tension transfer device is elastic and because the transfer of pressure to the urethral support portion 30 by contraction of the Retzius space caused by external pressure becomes smooth when the hardness of the material of the tension transfer device is about 70 Ha.

For example, if the hardness of the material of the device is low, external pressure will not be sufficiently transferred to the urethral support portion 30, and thus the urethral support portion 30 will not sufficiently apply pressure to the urethra 100. On the other hand, if the hardness of the material of the device is very high, there will be a problem in that the tension transfer device frequently moves in response to external pressure. Furthermore, if the hardness of the material of the tension transfer device is high, the wearing sensation of the tension transfer device will be significantly deteriorated to discomfort the patient, thus reducing the sense of trust for the solid material inserted into the body. For this reason, the hardness of the silicone material of the tension transfer device is preferably 10-90 Ha, and more preferably about 70 Ha, in terms of increasing the effect thereof.

As a result, the tension transfer device according to the embodiment of the present invention will sufficiently support the urethra upward through the method of transferring abdominal pressure using the hardness of the material and the shape of the device. As a result, the Retzius space-insertion portions 10 located in the Retzius spaces will act as rotating shafts which are fixed in the Retzius spaces by contraction of the Retzius spaces, while the fluid material filled in the device will move toward the urethral support portion 30 as shown in the figure to expand the urethral support portion 30, thereby supporting the urethra 100. Meanwhile, if the abdominal pressure is removed, the tension transfer device of the present invention will be returned to its original shape.

Figure 13:
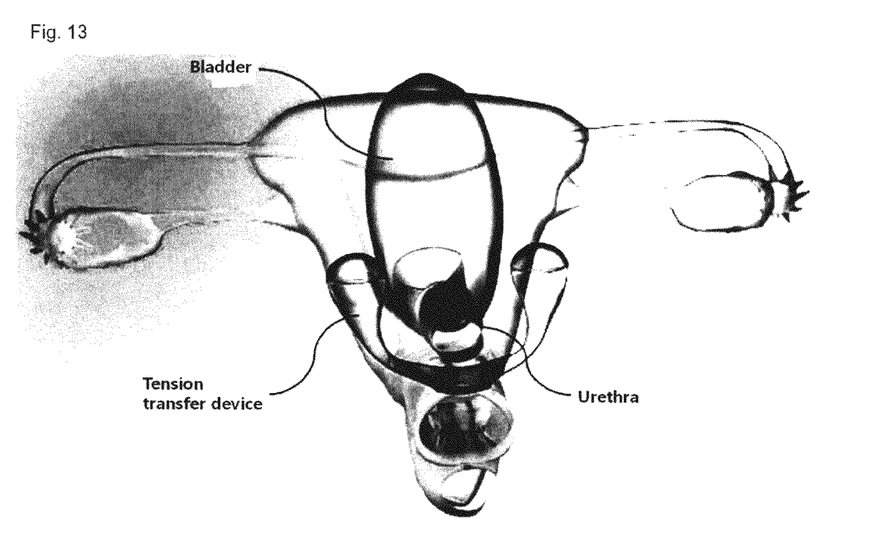
FIG. 13 illustrates a state in which the tension transfer device of the present invention was implanted into the human body.

FIG. 13 is a graphic showing that the tension transfer device according to the first embodiment of the present invention was inserted. As can be seen therein, as the tension transfer device is placed under the urethra, the urethral support portion 30 supports the urethra upward. Also, the Retzius space-insertion portions 10 are placed in Retzius spaces (not shown) which are brought into close contact with a certain position of the pelvis, for example, the inner side of the pubis. Thus, the Retzius space-insertion portions 10 of the tension transfer device support the back side of the pelvis, and the tension transfer device rotates with respect to the contact portion.

Meanwhile, where the tension transfer device according to the present invention is located in the Retzius spaces, the urethral support portion 30 that supports the urethra upward can follow the upward and downward oscillation of the Retzius spaces, which occur without regard to abdominal pressure when the patient exercises, for example, so that the force for supporting the urethra can be weakened. Namely, because there are also frequent cases in which urinary incontinence occurs due to the relaxation of muscles beneath the urethra, it is required to sufficiently support the urethra upward even when the Retzius spaces move upward and downward.

For this purpose, in each of the Retzius space-insertion portions 10 according to the present invention, an elasticity-attenuating opening 40 is formed so as to pass through the front lower portion and the side of the insertion portions. The elasticity-attenuating opening 40 is provided in a hook form in the each of the Retzius space-insertion portions 10, so that it attenuates the instantaneous downward movement of the Retzius spaces, thereby suppressing the downward movement of the urethral support portion 30.

Figure 6B:
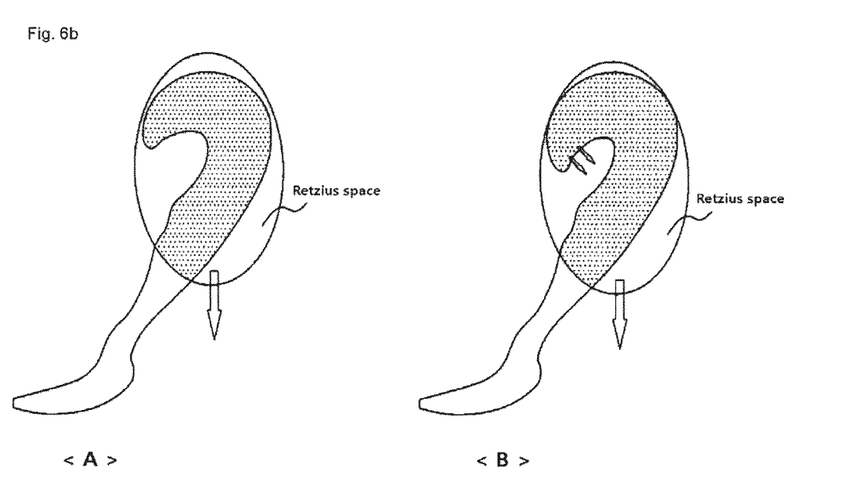

FIG. 6b illustrates the operation of the tension transfer device which occurs due to the upward and downward oscillation of the Retzius spaces. As shown therein, when the muscles of a urinary incontinence patient oscillate upward and downward due to severe physical exercise, the Retzius spaces will also oscillate together with the muscles. At this time, when the Retzius space moves downward as shown in "A" of FIG. 6b, the upper side of the Retzius space-insertion portion 10 comes into contact with the upper portion of the Retzius space, and as shown in "B" of FIG. 6b, the Retzius space-insertion portion 10 deflates the elasticity-attenuating opening 40, thereby reducing the elasticity of the Retzius space-insertion portion.

Namely, the downward movement of the Retzius space does not lead to the downward movement of the neck portion 20 and the urethral support portion 30, and the Retzius space-insertion portion 10 is bent at a certain angle due to the elasticity-attenuating opening 40. Namely, the Retzius space-insertion portion 10 elastically resists pressure caused by the movement of the Retzius space, so that the force of upward and downward movement of the Retzius space is not transferred to the urethral support portion 30 or is weakened. Thus, the urethral support portion 30 continuously elastically supports the urethra of the urinary incontinence patient upward when the patient exercises.

Figure 7:
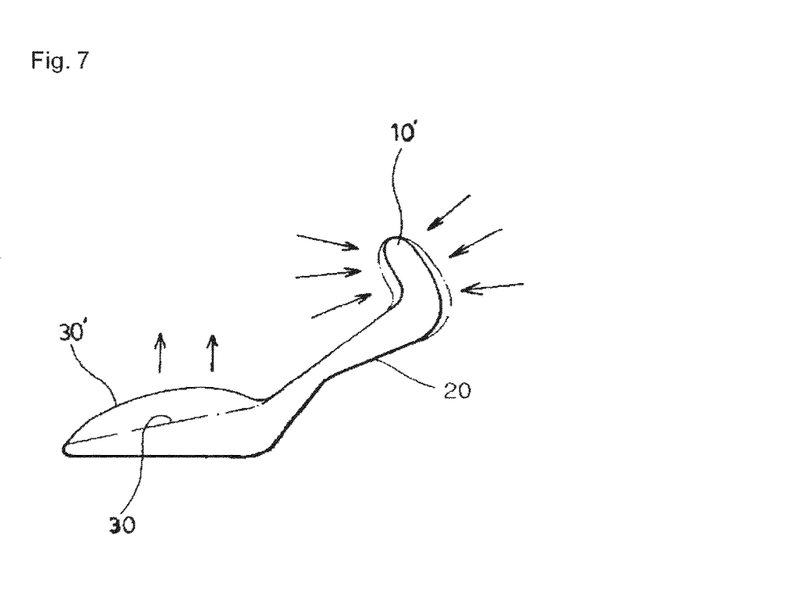
FIG. 7 imaginatively shows that, when the tension transfer device according to the first embodiment of the present invention is made of a solid material or includes a fluid material filled therein, it moves as abdominal pressure increases.
Figure 8:
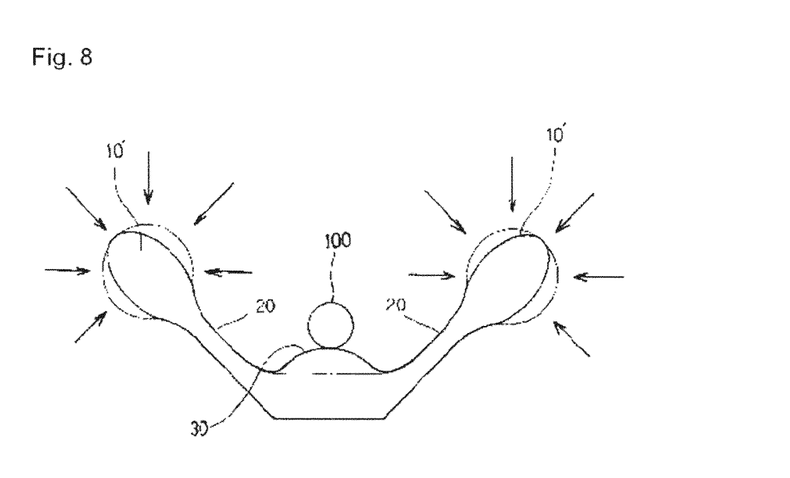
FIG. 8 is a front view of the tension transfer device shown in FIG. 7, which shows that the tension transfer device supports the urethra upward as abdominal pressure increases.

Meanwhile, although the tension transfer device according to the first embodiment of the present invention has been described as being formed of a silicone material, the tension transfer device may also be prepared by forming a silicone material into the shape of the device and then filling a fluid material therein to make a shape like a soft silicon bag containing saline. By doing so, in addition to using the elasticity of the silicone material itself, the change in shape resulting from the change in pressure caused by the compression of the Retzius space is efficiently induced. FIGS. 7 and 8 show that the tension transfer device containing the fluid material filled therein changes shape according to an increase in abdominal pressure.

Although the operational principle of this tension transfer device is identical to that of the tension transfer device according to the first embodiment of the present invention, the fluid material filled in this tension transfer device is used as a means for increasing the force for supporting the urethra upward. For this purpose, the tension transfer device can be designed such that it includes a sheath made of a silicone material, and a fluid material filled in the sheath and such that the material of the front portion of the urethral support portion 30 has lower hardness. Thus, through the deformation of the urethral support portion 30 by the fluid material together with the above-described rotating force provided with respect to the Retzius space-insertion portion 10, the force for supporting the urethra upward can be maximized.

If the abdominal pressure is removed, the tension transfer device will be returned to its original state due to its inherent elasticity, and thus the fluid material protruded from the surface of the urethral support portion 30 will also be returned to its original state. Examples of the fluid material that is filled in the tension transfer device according to the present invention include air, saline, cohesive gel and the like.

Figure 9:
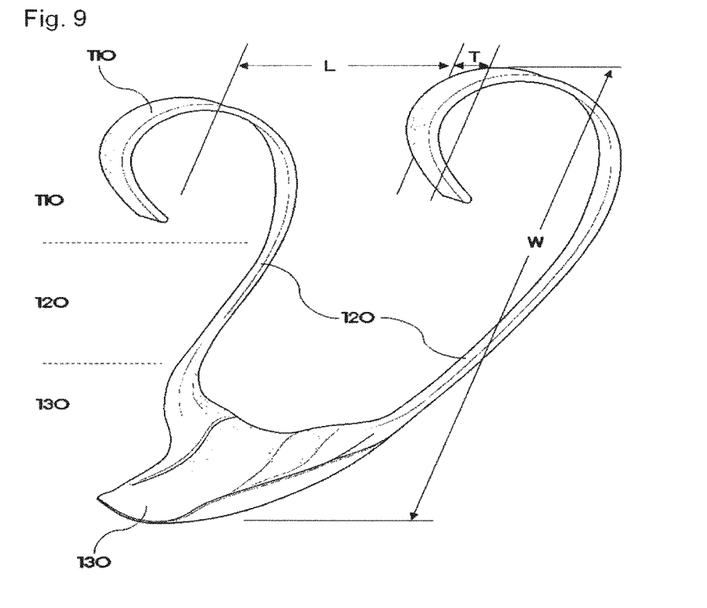
FIG. 9 is a perspective view of a tension transfer device according to a second embodiment of the present invention.

Meanwhile, FIG. 9 shows a tension transfer device according to a second embodiment of the present invention. As shown therein, the tension transfer device includes: a urethral support portion 130 which serves to support the urethra upward and is formed in such a manner than the lateral cross section thereof becomes thinner toward the distal end; neck portions 20 extending from both sides of the urethral support portion to Retzius spaces; and elasticity-attenuating portions 110, which are respectively inserted in Retzius spaces placed on the left and right sides of the urethra and serve to transfer a rotating force to the neck portions in response to the pressure of the Retzius spaces so that the urethral support portion moves upward toward the urethra, the elasticity-attenuating portions having a flat hook shape to attenuate the upward and downward oscillation of the Retzius spaces.

The urethral support portion 30 that serves to support the urethra upward preferably has a concave shape so as to be curved downward. However, the urethral support portion 30 may also have a convex shape so as to be curved upward. Alternatively, it may also be formed to have a flat shape having no curvature.

The tension transfer device according to this embodiment may be formed of a silicone material. Alternatively, it may be formed by forming a sheath made of a silicone material and filling therein a fluid material such as air, saline or cohesive gel.

Preferably, the urethral support portion 130, the neck portions 120 and the elasticity-attenuating portions 110 are formed to have an integral structure having the same hardness as that of the first embodiment as described above. Specifically, the tension transfer device according to this embodiment can be designed such that the material, hardness and dimension thereof are identical or similar to those of the first embodiment. As shown in the figure, the distance (L) between the two elasticity-attenuating portions 110 may be 1-100 mm, and preferably about 18-24 mm, and the width (W) between the uppermost side of any one of the elasticity-attenuating portions 110 and the lowest side of the urethral support portion 130 is 10-80 mm, and preferably 30-35 mm.

Also, the width (T) of each of the elasticity-attenuating portions 110 having a flat structure may be 2-50 mm, and preferably about 10-15 mm. Moreover, the thickness (t) of the elasticity-attenuating portion 110 is 1-5 mm, and preferably 1-1.5 mm. Meanwhile, this tension transfer device may be made of a silicone elastic material, an elastic material harmless to the human body, or a sheath material containing a fluid material, and have a hardness of about 10-90 Ha, and preferably about 70 Ha (1.925 N).

Also, in this embodiment, the neck portion 120 and the urethral support portion 130 are provided at a slope ($\theta$) of 120-140°, but it is to be understood that they can be formed at an angle of 30-170° in consideration of the elasticity of the material. This hardness value of silicone is an experimentally determined value that maintains psychological stability by offsetting sensations caused by adhesion of the silicone to human tissue when the silicon is inserted into the human body. Thus, the hardness of silicone can be suitably selected within the range in which it is harmless to the human body.

In addition, the fluid material-containing sheath material of the tension transfer device according to this embodiment is provided as a means for realizing the tension transfer device. It should be noted that the fluid material-containing sheath material does not serve to induce the protrusion shape from the urethral support portion 130, unlike the description of the first embodiment.

After the tension transfer device according to this embodiment has been implanted into a urinary incontinence patient, if the abdominal pressure increases when the patient exercises, sneezes, coughs or laughs, the pressure of the Retzius spaces positioned on the left and right sides of the urethra will also increase. At the same time, the muscles around the urethra will also tense to increase the pressure of the Retzius spaces.

Figure 10A:
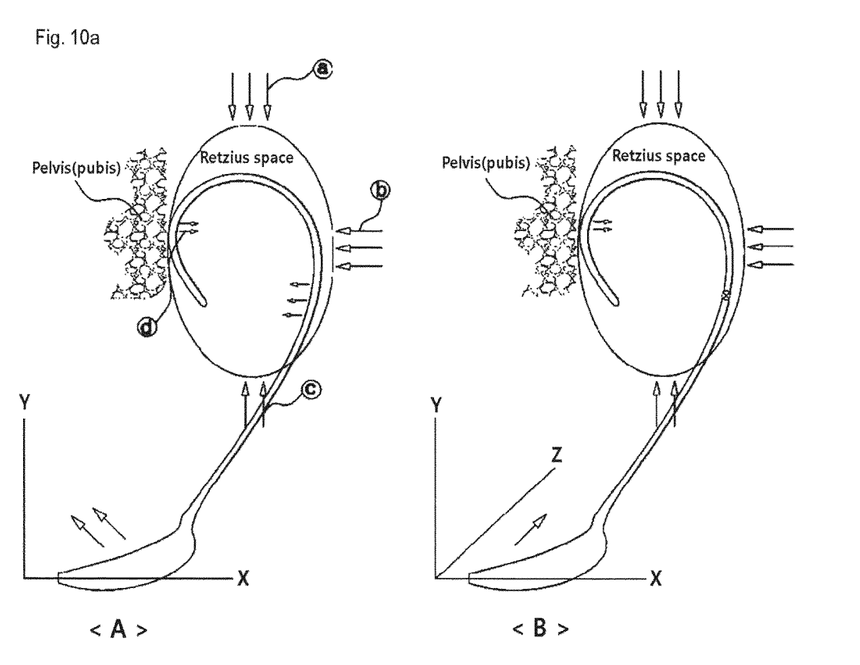
FIGS. 10a and 10b are views illustrating the main operational principle of the tension transfer device according to the second embodiment of the present invention.

Specifically, as shown in "A" of FIG. 10a, the neck portion 120 is pressed from the direction of the x-axis to the y-axis with respect to the front upper portion of the elasticity-attenuating portion 110 which is pressed by the Retzius space. When the Retzius space located between the pelvis (pubis) and the bladder is contracted in the x-axis and y-axis directions, the Retzius space is pressed at a certain position of the pelvis. In this regard, the contact point between the pelvis and the Retzius space acts as a hinge point, and by the pressure that is applied downward to the Retzius space, the urethral support portion 30 rotates clockwise with respect to the figure. Specifically, as shown in the figure, when muscles contract, external pressures ⓐ, ⓑ and ⓒ are applied to the Retzius space. In this regard, the forces corresponding to the forces ⓐ and ⓑ are substantial forces caused by muscles, and the force corresponding to the force ⓒ is an indirect force caused by muscular contraction. Thus, the forces ⓐ and ⓒ are somewhat offset, and then the downward pressure remains. The force ⓑ is attenuated by action and reaction (force corresponding to ⓓ) for the pelvis (pubis).

However, an external force such as the force ⓑ acts between the elasticity-attenuating portion 110 and the neck portion 20 or on a part of the neck portion 20. As a result, the force ⓑ acts in the negative (−) direction of the x-axis, while the forces ⓐ and ⓒ act in the negative (−) direction of the y-axis from the composition of forces. Thus, the elasticity-attenuating portion 110 receives a force in the direction of the left and down side of the figure. Also, as the contact point between the elasticity-attenuating portion 110 and the pelvis (pubis) acts as a hinge point, the neck portion 20 rotates clockwise in the figure.

In addition to this rotating force, as shown in "B" of FIG. 10a, an external force that presses the outer portion of the neck portion 20 can partially exist, which can add a force that rotates the urethral support portion 30, extending to the neck portion 20, in the direction from the x-axis to the z-axis. Thus, with this operational principle, the urethral support portion 30 having a concave curved portion will press the urethra upward and prevent urinary incontinence due to the force for supporting the urethra upward.

Figure 10B:
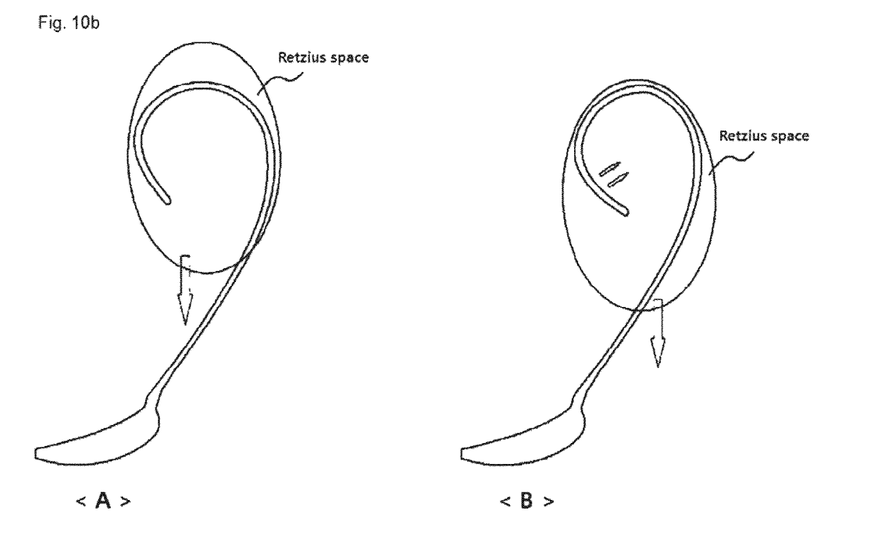

FIG. 10b illustrates the operation of the tension transfer device, which occurs due to the upward and downward oscillation of the Retzius spaces. As shown therein, when the muscles of a urinary incontinence patient oscillate upward and downward due to severe physical exercise, the Retzius spaces will also oscillate together with the muscles. At this time, when the Retzius space moves downward as shown in "A" of FIG. 10b, the upper side of the elasticity-attenuating portion 110 comes into contact with the upper portion of the Retzius space, and as shown in "B" of FIG. 10b, the elasticity-attenuating portion 110 is contracted, thereby reducing the elasticity of the device. Thus, in this embodiment, based on the same principle as the above-described first embodiment, the urethral support portion 130 will sufficiently support the urethra upward even when the Retzius spaces move upward and downward.

Figure 11:
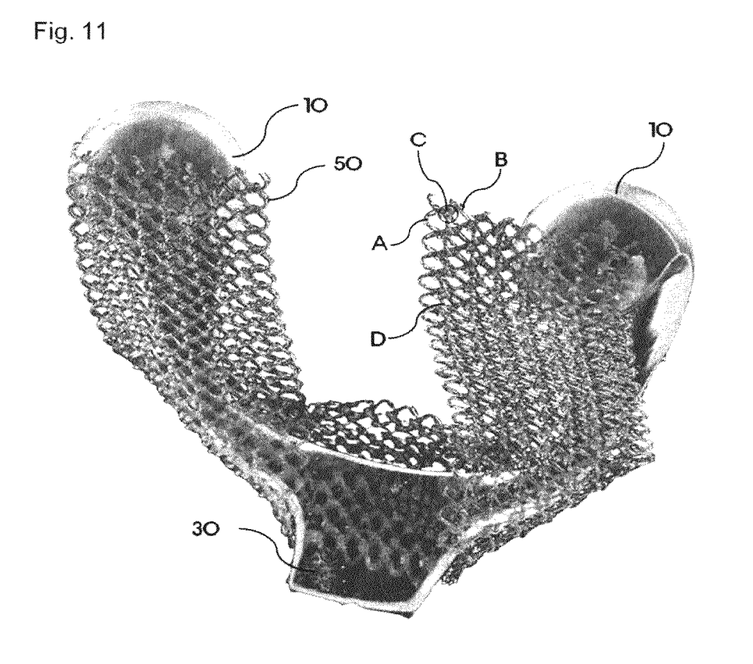
FIG. 11 is a perspective view of a tension transfer device according to a third embodiment of the present invention.

FIG. 11 shows a photograph of a tension transfer device according to a third embodiment of the present invention. The tension transfer device according to this embodiment has a structure in which the tension transfer device according to the first embodiment of the present invention is combined with a mesh structure. However, it is to be understood that the tension transfer device according to the second embodiment can be combined with the mesh structure to be described below and that this combination structure will also be included within the scope of the present invention.

Reference numerals for the structure of this embodiment will be described based on the reference numerals shown in the first embodiment. As shown in FIG. 3, the tension transfer device according to this embodiment includes: a urethral support portion 30 which serves to support the urethra upward and is formed such that the lateral cross section thereof becomes thinner toward the distal end; neck portions (20; reference numeral omitted) extending from both sides of the urethral support portion 30 to Retzius spaces; Retzius space-insertion portions 10 which are respectively to be inserted in the Retzius spaces positioned on the left and right sides of the urethra and serve to transfer a rotating force to the neck portions in response to the pressure of the Retzius spaces so that the urethral support portion moves upward toward the urethra, the Retzius space-insertion portions each having an elasticity-attenuating opening (40; reference numeral omitted) so as to attenuate the upward and downward oscillation of the Retzius spaces; and a mesh structure 50 which surrounds the backside of the urethral support portion and each of the neck portions in a 'U' shape and is partially thermally bonded to the backside of the urethral support portion and each neck portion.

In this embodiment, the lateral cross section of the urethral support portion is formed such that it becomes thinner from the Retzius space-insertion portion toward the distal end.

Also, the urethral support portion 30 that serves to support the urethral upward preferably has a concave shape so as to be curved downward. Alternatively, the urethral support portion 30 may have a convex shape so as to be curved upward or may be formed to have a flat structure having no curvature.

The mesh structure 50 has a network structure made of polypropylene and can extend from the urethra to the end of the Retzius space. Thus, the mesh structure 50 may have a length of about 5-200 mm, but the length is preferably determined such that the end of each of the structures in which the mesh structure 50 surrounds the neck portion 20 in the 'U' shape does not pass by the Retzius space-insertion portion 10.

If the mesh structure 50 has a length of about 5 mm, for example, 5-10 mm, it cannot surround the neck portion 20. This is because, when the mesh structure 50 is inserted into the human body, it will be adsorbed onto the human tissue and fixed to the human tissue. For this reason, in this embodiment, the tension transfer device can be used in such a manner that the mesh structure 50 is attached to the lower surface of the urethral support portion 30 or surrounds a portion of the urethral support portion 30.

If the mesh structure 50 has a short length, it may be thermally bonded to the lower surface of the urethral support portion 30 or may be inserted into a groove (not shown) formed on the lower surface of the urethral support portion 30.

As a result, the length at which the mesh structure 10 surrounds the neck portion 20 may be 10-200 mm, and the length at which the mesh structure 50 is bonded to or inserted into the lower surface of the urethral support portion 30 may be 5-10 mm.

The mesh structure 50 is prepared by combining the sides of meshes with each other to form a woven fabric using a knitting machine.

Specifically, meshes formed at the side of one mesh line A and meshes formed at the side of another mesh line B corresponding thereto are combined with each other, and thus the combined meshes are linearly arranged at the center of a connection C. Also, a simple thread-shaped single strand D is provided to combine the meshes with each other.

The meshes are lozenge-shaped, and the diagonal line of the lozenge is 1.5 mm or less. This mesh structure is a single layer structure and has a thickness of 0.5-1 mm, and preferably about 0.7 mm. When this mesh structure is inserted into the human body, it has strong adhesion to the human tissue. Also, the mesh structure 50 may be made completely of polypropylene. If necessary, the mesh structure may also be made of Avcothane (a polyether urethane/polydimethylsiloxane blend), a styrene/polyamine copolymer, or a segmented polyurethane/silicone rubber blend. Thus, the mesh structure 50 prevents relaxation of tissue in the human body, that is, induces the tension of the muscles around the urethra, thereby contributing to reducing urinary incontinence.

If the tension transfer device comprising the mesh structure 50 is implanted into a urinary incontinence patient, when the patient exercises, sneezes or coughs to increase the abdominal pressure instantaneously, the urethral support portion 30 will press the urethra due to the increase in the pressure of the Retzius spaces, while the mesh structure 50 usually induces the tension of the muscles around the urethra, thereby inhibiting involuntary urinary incontinence caused by muscular relaxation.

As a result, the tension transfer device together with the mesh structure 50 significantly reduces urinary incontinence and induces continuous tension of the muscles around the urethra. This tension transfer device according to the present invention is implanted through simple surgery by incising a minimum area of a region beneath the urethra and inserting the Retzius space-insertion portions into the Retzius spaces, and thus it does not require a guide needle holder that causes damage, unlike the prior art. Also, it is minimally invasive, so that damage associated with the prior invasive surgery method can be significantly reduced. In addition, it is easily removed, and thus it makes it possible to perform surgery again using another method when it is not effective for treatment.

In addition, the tension transfer devices according to the first to third embodiments of the present invention were implanted into urinary incontinence patients in small clinical trials. As a result, the patients could feel no foreign-body sensation of the tension transfer device, and expressed satisfaction about the treatment of urinary incontinence. Also, the medical specialists confirmed that spinal anesthesia, sedative anesthesia or the like was not required in the surgical procedure and that the device did not cause discomfort which can occur when excessive local anesthesia is performed.

The invention claimed is:

1. An infra-obturator tension transfer device comprising: a urethral support portion which is adapted to support an urethra upward and is formed such that a lateral cross section thereof becomes thinner toward a distal end; neck portions extending from a left side and a right side of the urethral support portion adapted to extend toward Retzius spaces; and Retzius space-insertion portions which are respectively adapted to be inserted in the Retzius spaces positioned on a left side and a right side of the urethra such that said Retzius space-insertion portions serve as an axis of rotation and transfer a rotating force to the neck portions in response to a pressure of the Retzius spaces so that the entire urethral support portion moves upward toward the urethra, the Retzius space-insertion portions each having an elasticity-attenuating opening so as to attenuate an upper and lower oscillation of the Retzius spaces, wherein each of the Retzius space-insertion portions has a diameter (2R) of 5-40 mm, a distance (L) between the Retzius space-insertion portions is 1-100 mm, a width (W) between an uppermost side of any one of the Retzius space-insertion portions and a lowest side of the urethral support portion is 10-80 mm, wherein the infra-obturator tension transfer device has an angle of 30-170 between each of the neck portions and the urethral support portion.

2. The infra-obturator tension transfer device of claim 1, wherein the urethral support portion has any one of a downwardly curved concave shape, and an upwardly curved convex shape.

3. The infra-obturator tension transfer device of claim 1, wherein each of the Retzius space-insertion portions has a diameter (2R) of 8-11 mm, the distance (L) between the Retzius space-insertion portions is 18-24 mm, the width (W) between the uppermost side of any one of the Retzius space-insertion portions and the lowest side of the urethral support portion is 30-35 mm, wherein said angle is 120-140°.

4. The infra-obturator tension transfer device of claim 1, wherein the tension transfer device is formed of a silicone material and has a hardness of 10-90 Ha.

5. The infra-obturator tension transfer device of claim 1, wherein the tension transfer device is formed of any one of a silicone elastic material, an elastic material harmless to a human body, and a sheath material containing a fluid material, and has a hardness of 10-90 Ha.

6. The infra-obturator tension transfer device of claim 1, wherein the axis of rotation is offset from the urethral support portion.

7. An infra-obturator tension transfer device comprising: a urethral support portion adapted to support a urethra upward and is formed such that a lateral cross section thereof becomes thinner toward a distal end; neck portions extending from a left side and a right side of the urethral support portion and adapted to extend toward Retzius spaces; and sphere-shaped Retzius space-insertion portions which are respectively adapted to be inserted in the Retzius spaces positioned on a left side and a right side of the urethra such that said Retzius space-insertion portions serve as an axis of rotation and transfer a rotating force in response to a pressure of the Retzius spaces to the neck portions so that the urethral support portion move upward toward the urethra, wherein each of the Retzius space-insertion portions has a diameter (2R) of 5-40 mm, a distance (L) between the Retzius space-insertion portions is 1-100 mm, a width (W) between an uppermost side of any one of the Retzius space-insertion portions and a lowest side of the urethral support portion is 10-80 mm, wherein the infra-obturator tension transfer device has an angle of 30-170 between each of the neck portions and the urethral support portion.

8. An infra-obturator tension transfer device comprising:
a urethral support portion which is adapted to support a urethra upward and is formed such that a lateral cross section thereof becomes thinner toward a distal end;
neck portions extending from a left side and a right side of the urethral support portion adapted to extend toward Retzius spaces;
Retzius space-insertion portions which are respectively adapted to be inserted in the Retzius spaces positioned on a left side and a right side of the urethra such that said Retzius space-insertion portions serve as an axis of rotation and transfer a rotating force to the neck portions in response to a pressure of the Retzius spaces so that the entire urethral support portion moves upward toward the urethra, the Retzius space-insertion portions each having an elasticity-attenuating opening so as to attenuate an upward and downward oscillation of the Retzius spaces; and
a mesh structure which surrounds a backside of the urethral support portion and each of the neck portions in a 'U' shape and is partially thermally bonded to the backside of the urethral support portion and each neck portion.

9. The infra-obturator tension transfer device of claim 8, wherein the mesh structure has a woven mesh structure having a length of 10-200 mm.

10. The infra-obturator tension transfer device of claim 8, wherein the urethral support portion has any one of a downwardly curved concave shape, an upwardly curved convex shape, and a flat shape having no curvature.

11. The infra-obturator tension transfer device of claim 8, wherein each of the Retzius space-insertion portions is sphere shaped and has a diameter (2R) of 5-40 mm, a distance (L) between the Retzius space-insertion portions is 1-100 mm, a width (W) between an uppermost side of any one of the Retzius space-insertion portions and a lowest side of the urethral support portion is 10-80 mm, wherein the infra-obturator tension transfer device has an angle of 30-170° between each of the neck portions and the urethral support portion.

12. The infra-obturator tension transfer device of claim 11, wherein each of the Retzius space-insertion portions has a diameter (2R) of 8-11 mm, the distance (L) between the Retzius space-insertion portions is 18-24 mm, the width (W) between the uppermost side of any one of the Retzius space-insertion portions and the lowest side of the urethral support portion is 30-35 mm, and wherein said angle is 120-140°.

13. The infra-obturator tension transfer device of claim 8, wherein the tension transfer device is formed of a silicone material and has a hardness of 10-90 Ha.

14. The infra-obturator tension transfer device of claim 8, wherein the tension transfer device is formed of any one of a silicone elastic material, an elastic material harmless to a human body, and a sheath material containing a fluid material, and has a hardness of 10-90 Ha.

15. The infra-obturator tension transfer device of claim 8, wherein the mesh structure is a woven mesh structure made of any one of polypropylene, a polyether urethane/polydimethylsiloxane blend, a styrene/polyamine copolymer, and a segmented polyurethane/silicone rubber blend.

* * * * *